United States Patent [19]

Martin et al.

[11] Patent Number: 4,668,216
[45] Date of Patent: May 26, 1987

[54] SYSTEM FOR MOUNTING A DROP SENSOR TO A DRIP CHAMBER

[75] Inventors: Stephen A. Martin, Carlsbad; Terry L. Landis, San Diego; Richard A. Bizzigotti, San Marcos, all of Calif.

[73] Assignee: Ivac Corporation, San Diego, Calif.

[21] Appl. No.: 710,044

[22] Filed: Mar. 11, 1985

[51] Int. Cl.⁴ ............................................. A61M 1/00
[52] U.S. Cl. ........................................ 604/30; 604/67; 604/246; 604/253
[58] Field of Search ...................... 604/30, 31, 65–67, 604/246, 251–254

[56] References Cited

U.S. PATENT DOCUMENTS

| 3,500,366 | 3/1970 | Chesney et al. | |
| 4,038,982 | 8/1977 | Burke et al. | |
| 4,237,878 | 12/1980 | Kobayashi et al. | 604/253 |
| 4,321,461 | 3/1982 | Walter et al. | |
| 4,346,606 | 8/1982 | Cannon et al. | |
| 4,397,648 | 8/1983 | Knute | |
| 4,533,350 | 8/1985 | Danby et al. | 604/253 |

FOREIGN PATENT DOCUMENTS 1252615  11/1971  United Kingdom ............... 604/253

Primary Examiner—Stephen C. Pellegrino
Assistant Examiner—Mark Rooney
Attorney, Agent, or Firm—Fulwider, Patton, Rieber, Lee & Utecht

[57] ABSTRACT

The invention is directed to an improved system for mounting a drop sensor onto a drip chamber having laterally projecting wing-like or flange-like extensions. A pair of mounting members, one fixed, one laterally movable, are provided on the drop sensor housing. The mounting members have inclined guiding surfaces which cradle both ends of the lateral extensions on the drip chamber during the initial stages of mounting the drop sensor to the drip chamber and guide drop sensor movement with respect to the drip chamber to its final mounted position thereon. The mounting system is particularly adapted to dedicated IV set and drop sensor combinations.

19 Claims, 10 Drawing Figures

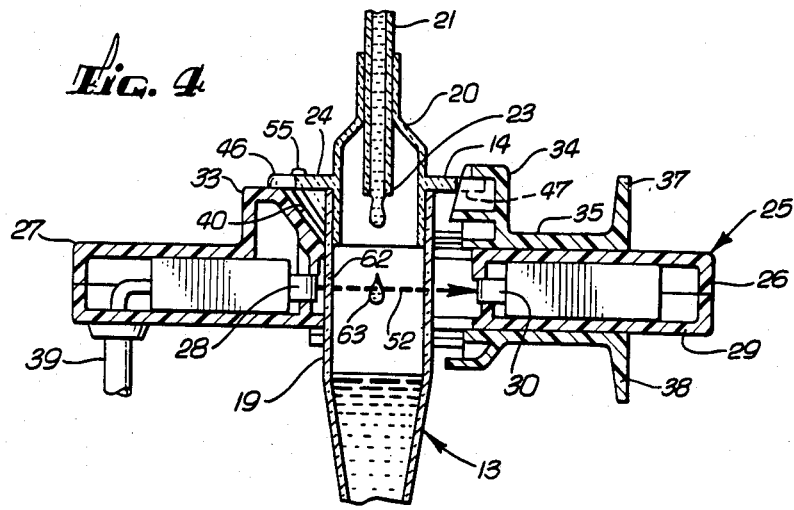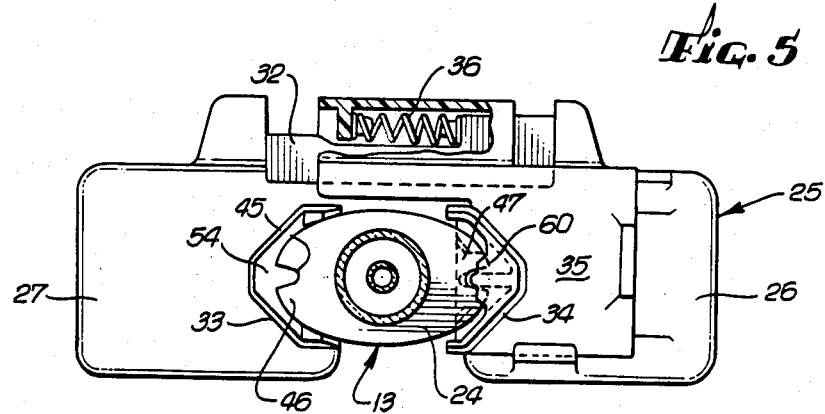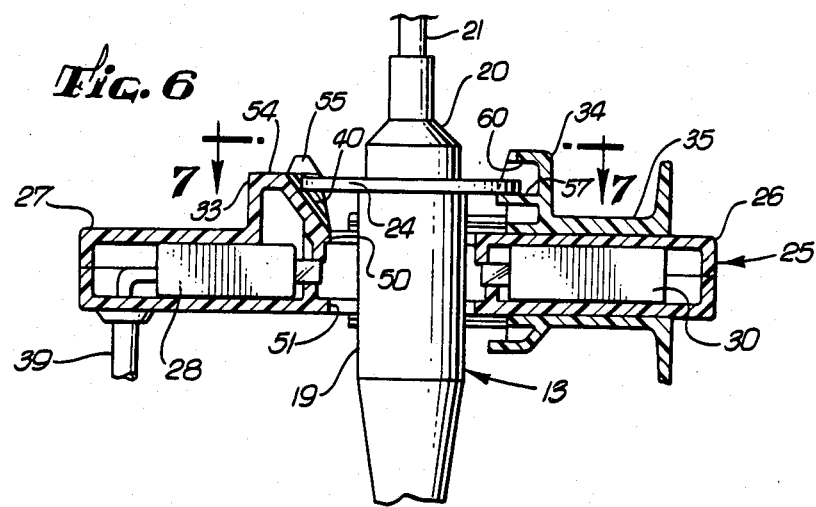

SYSTEM FOR MOUNTING A DROP SENSOR TO A DRIP CHAMBER

BACKGROUND OF THE INVENTION

This invention generally relates to the administration of parenteral fluids to a patient by means of an intravenous (IV) set and particularly to an improved means for mounting a drop sensing unit to a drip chamber dedicated to the particular IV delivery instrument.

An IV set for the administration of parenteral fluids generally comprises a drip chamber, a length of clear plastic tubing attached to the discharge end of the drip chamber, one or more clamps to adjust the fluid flow through the clear plastic tubing and a means at the distal end of the tubing for mounting a hypodermic needle which will be inserted into the patient's vein or artery. The drip chamber is generally cylindrically shaped and is provided with a pointed hollow element (i.e., piercing element) at the top thereof which is adapted to pierce the rubber or elastomeric seal on an inverted bottle of parenteral fluid in order to drain the fluid therefrom into the drip chamber. The cylindrical wall of the drip chamber is formed from clear plastic material in order to detect fluid dripping into the chamber.

Fluid flow to the patient is usually determined by detecting the number of drops of fluid which fall into the drip chamber over a period of time and then multiplying the number of drops by a standard number used for the volume of each drop. When this method of flow rate detection is done manually, it is time consuming and frequently inaccurate.

Effective instrumentation for monitoring the drop rate into a drip chamber has been developed which comprises a light source which is positioned on one side of the clear plastic wall of the drip chamber and a photoelectric cell or other light sensor on the opposite side of the chamber wall with a light path therebetween so that the drops of parenteral fluid falling into the drip chamber intersect the light path and are thereby sensed.

With the need for greater accuracy in the delivery of parenteral fluids, particularly when drugs have been added to the fluid, the drop forming elements of the drip chamber are now carefully designed and manufactured so that the size and dropping characteristics of the fluid drops are relatively constant over a period of time and do not vary greatly from drip chamber to drip chamber. To insure that drip chambers of known drop characteristics are used with a particular IV delivery instrument, the means for coupling the drop rate monitor to the drip chamber have been designed so that only matched sets can be used together. Such mounting or coupling means are described in the following list of patents which is illustrative but not exhaustive.

U.S. Pat. No. 4,397,648 (Knute)
U.S. Pat. No. 4,346,606 (Channon et al.)
U.S. Pat. No. 4,321,461 (Walter et al.)
U.S. Pat. No. 4,038,982 (Burke et al.)
U.S. Pat. No. 3,500,366 (Chesney et al.)

However, by making the mounting element unique so that only matched components can be used together, the mounting has become more complicated and more difficult to operate, particularly in low light or in emergency situations when visual accuity may not be great.

Knute, in U.S. Pat. No. 4,397,648 (assigned to the present assignee) discloses an improved mounting system which insured proper positioning of the drop sensor on the drip chamber and which had self-aligning characteristics. However, even though the mounting system developed by Knute was a substantial advance, the mounting system was not convenient in many situations and correct positioning of the drop sensor was not always effected the first time mounting was attempted. Moreover, once the sensor was mounted the sensor was subject to misalignment or displacement by accidental contact with the sensor, the drip chamber or other parts of the IV set during use.

Thus there remains a need for a drop sensing unit which can easily and accurately be positioned onto a dedicated drip chamber, which has more dependable self-aligning characteristics and which is less apt to become misaligned during use due to accidental contact with the sensor, the drip chamber or other components of the IV set. The present invention satisfies this need.

SUMMARY OF THE INVENTION

This invention generally relates to an improved system for monitoring the flow of parenteral fluid through a fluid administration set to a patient and is specifically directed to an improved system for mounting a drop sensor to a drip chamber.

The drip chamber in accordance with the invention is provided with a clear plastic, cylindrically shaped body and a pair of opposed lateral projections which facilitate mounting the drop sensor thereon.

The drop sensor, which is adapted to encircle a substantial portion of the drip chamber body, has a pair of mounting members, one of which is fixed and one of which is laterally movable. Each of the mounting members has one or more inclined guiding surfaces which cradle the opposing lateral extensions during the initial stages of mounting. The movable mounting member is urged inwardly so that the inclined surfaces cradling the lateral extension slide over the edges thereof to effect relative movement therebetween. The included surfaces guide the mounting members relative to the lateral extension so that the positioning elements on the mounting members will firmly engage the lateral extensions. Additionally, the drop sensor housing contacts the cylindrical wall of the drip chamber at one or more points vertically disposed from the contact between the lateral extensions and the mounting members. These three areas of contact provide positive positioning of the drop sensor onto the drip chamber.

The drop sensor is provided with a housing having two separate sections, one section having a light source and one section having a light sensor, with a sensor gap disposed between the two sections which allows the sections to be disposed on opposing sides of the cylindrical body of the drip chamber. The two mounting members are positioned on top of the sensor housing sections.

The laterally movable mounting member is formed in a unitary structure with a sleeve which is adapted to slidably mounted to the sensor housing and which is provided with one or more finger engaging elements to facilitate the lateral sliding movement of the sleeve over the housing and thus the lateral movement of the moveable mounting member thereon. The sleeve is preferably spring loaded to close toward the fixed mounting member. When the sleeve is moved laterally away from the fixed mounting member for mounting, the maximum distance across the sensor gap between the inclined guiding surfaces of the two mounting means must be greater than the distance between the ends of the two cantilevered extensions on the drip chamber to ensure that both ends of the wing-like or flange-like extensions on the drip chamber are cradled by the inclined surfaces on the mounting means when the drip chamber is positioned within the sensor gap. Upon release of the spring loaded sleeve member, the inclined camming surfaces on the mounting members slide over the edges of the lateral extensions effecting relative vertical and horizontal movement between the drip chamber and drop sensor. The positioning elements on top of the mounting member are brought into engagement with the lateral extension and the sensor housing is brought into contact with the clear plastic, cylindrical wall of the drip chamber at one or more places thereby. In this manner, the sensor housing mounted on the drip chamber is aligned so that the drops of fluid dripping into the chamber intersect the optical pathway between the light source and light sensor.

In a preferred embodiment, the movable mounting member is provided with an overhang at the upper end of the inclined surfaces which is adapted to engage the upper surface of the lateral extension on the drip chamber and to thereby stop the relative vertical movement of the laterally moving mounting member with respect to the drip chamber extension.

In another preferred embodiment, the movable mounting member is provided with two or more outer inclined camming surfaces and a centrally located projecting guide element or rib which is adapted to ride in the groove or notch provided in the end of the extension in contact therewith. The notch and the rib are shaped to match. The outer camming surfaces are adapted to properly cradle the end of the lateral extension of the drip chamber in contact therewith so that the projecting guide therebetween slides in the notches provided in the ends and guides the overhang to engage the top surface of the lateral extension and to stop relative vertical movement therebetween. These features are particularly important in the use of IV sets designed for use with a specific drop sensor which has been calibrated for the drop size and/or shape formed by the drop former in the dedicated drip chamber. The mating elements on the mounting means, i.e., the rib, nothces and camming surfaces, ensure that only matched components are used together.

In another preferred embodiment, the fixed mounting member is provided with a conically shaped camming surface which is inclined away from the longitudinal axis of the drip chamber in the upward direction and which leads to a plateau atop the mounting member. The plateau is provided with vertically oriented stopping surfaces to prevent relative movement in a horizontal plane between the extension and the mounting member. When mounting the drop sensor, the clamping force applied by the spring loaded mounting member causes relative sliding movement between the inclined conical surface and the edges of the lateral extension of the drip chamber until the upper plateau moves under the lateral extension.

To couple the sensor to the drip chamber in accordance with the invention, the spring loaded sleeve with the movable mounting member is pulled laterally away from the fixed mounting member, the sensor housing is positioned around the drip chamber with the cylindrical body of the drip chamber disposed within the sensing gap and with both ends of the lateral extensions of the drip chamber being cradled by the inclined camming surfaces on both the fixed and movable mounting members. The spring loaded sleeve is released thereby causing the inclined guiding surfaces to slide under the edges of the extensions until the positioning elements on both mounting members engage the ends of the extensions to fix the relative positions thereon. Simultaneously, a housing section, preferably the section having the light sensor vertically spaced from the mounting members, is urged into contact with the clear plastic wall of the drip chamber body. The drop sensor is thus positioned so that the drops of fluid dripping into the drip chamber properly intersect the light path and are thereby detected.

As is evident, the mounting system in accordance with the present invention is very simple and, because vertical, horizontal and rotational movement between the drop sensor and the drip chamber is restricted, there is considerably less chance of misalignment of the sensor on the drip chamber due to accidental contact. Moreover, because of the mating elements provided with the mounting means only matched sets of drip chambers and drop sensors will be coupled together.

These and other advantages will become more apparent from the following detailed description when taken in conjunction with the accompanying drawings.

BRIEF DESCRIPTION OF THE DRAWINGS

FIG. 4 is an elevational view in section of the sensor unit mounted on the drip chamber as shown in FIG. 1;

FIG. 5 is a top view, partially in section, illustrating the drop sensor mounted on the drip chamber as shown in FIG. 4;

FIG. 6 is an elevational view, partially in section, illustrating the initial stages of mounting the drop sensor to the drip chamber;

DETAILED DESCRIPTION OF THE INVENTION

Figure 1:
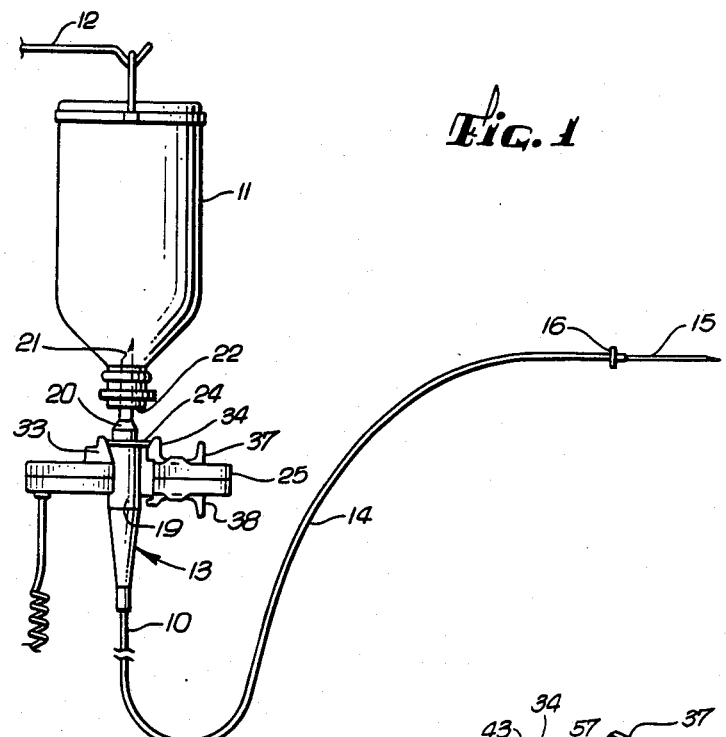
FIG. 1 is an elevational view of an IV set provided with a drip chamber and a drop sensor which embody features of the invention.
Figure 2:
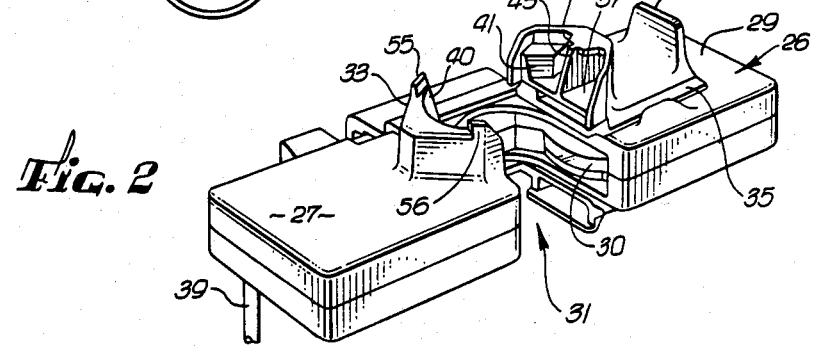
FIG. 2 is a perspective view on a larger scale of the drop sensor shown in FIG. 1.
Figure 3:
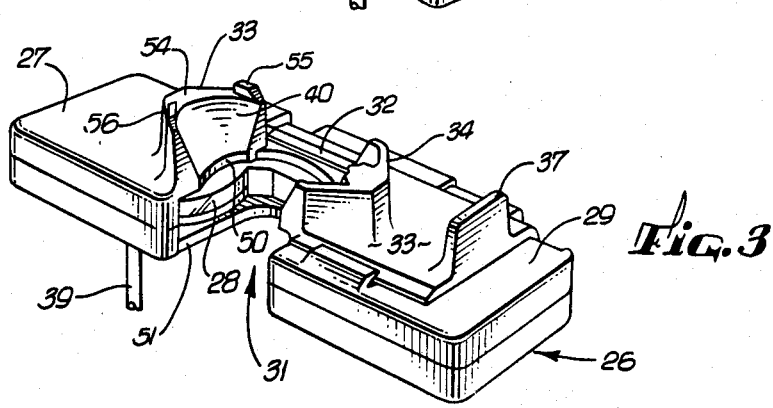
FIG. 3 is another perspective view of the drop sensor shown in FIG. 1.

Reference is made to FIG. 1 which illustrates an IV set 10 embodying features of the invention. The IV set 10 is connected to an inverted bottle 11 containing parenteral fluid hanging from the arm 12 of an IV stand (not shown). The IV set 10 as illustrated comprises a drip chamber 13, clear plastic tubing 14, needle 15 and mounting means 16 therefor at the distal end of tubing 14. Other common IV components such as Y-injection sites, roll clamps, filters and the like have not been shown in the drawings in order to keep them as simple as possible.

The drip chamber 13 generally comprises a clear plastic, hollow, cylindrical body 19, an upper portion 20 provided with a pointed piercing element 21 adapted to be inserted through the piercable seal 22 in the top of the bottle 11 to drain the fluid therein through drop former 23 when the bottle 11 is in an inverted position and hung from the arm 12 as shown, and lateral extensions 24 which aid in pushing the piercing element 21 through seal 22 and which facilitate mounting the drop sensor 25 to drip chamber 13 in accordance with the invention.

As shown in FIGS. 2-10 drop sensor 25 comprises an elongated housing 26, a first housing section 27 which is provided with a light sensor 28, a second housing section 29 which is provided with a light source 30 and a sensor gap 31 between the two sections into which the drip chamber 13 fits when the drop sensor 25 is mounted thereon. The sections 27 and 29 are joined together by means of a bridge 32 to integrate the housing 25 into a single unit. A fixed mounting member 33 is provided on section 27 and a movable mounting member 34, which is formed integrally with a sleeve 35, is slidably mounted on housing 26. The sleeve 35 is spring loaded to close as shown in FIG. 5 by means of spring 36 and is provided with a pair of finger gripping elements 37 and 38 to facilitate the lateral movement of the sleeve 35 on the housing 26 during the mounting of drop sensor 25 to the drip chamber 13. The fixed mounting member 33 is provided with a conically shaped inclined guiding or camming surface 40. Movable mounting member 34 is provided with inclined or camming surfaces 41 and 42 for contact with the edges of lateral extension 24 and an inclined projecting guide element or rib 43 which is adapted to interfit and mate with the matched notches 44 and 45 provided in the ends 46 and 47 of extensions 24. Both of the ends 46 and 47 are notched so that the drop sensor 25 can be mounted from either side of the drip chamber 13. In this manner, only a drop sensor which is matched to the drip chamber 13 can be mounted on the drop chamber. While only one rib 43 and a mating notch 44 are shown, several ribs and matched notches may be used to provide even greater assurance that only dedicated IV set and drop sensor combinations will be used together.

FIG. 4 illustrates a sectional view of the drop sensor 25 mounted onto the drip chamber 13 with the mounting members 33 and 34 engaging the ends 46 and 47 of the cantilevered extensions 24, and vertical support surfaces 50 and 51 contacting the cylindrical body 20 of the drip chamber 13 to thereby fix the position of sensor 25 with respect to the drip chamber 13. Surface 50 preferably conforms to the circular shape of the cylindrical body 20. Surface 51, while helpful in firmly positioning the sensor 25 to the drip chamber 13, is not necessary. Section 27 of housing 26 contains a light sensor 28 and the second section 29 contains a light source 30. A light path 52 crosses the sensor gap 31 through body 20 of drip chamber 13 between the light source 30 and the light sensor 28. A cable 39 is provided to transmit signals from the light sensor 28 to control means, alarms or the like which are not shown and also to provide electrical power to the light source.

The inclined guiding surfaces 40-43 and the positioning means atop the mounting members 33 and 34 are best illustrated in FIGS. 3, 6, 7 and 8. The conically shaped camming surface 40 on mounting member 33 diverges in the upward direction away from the vertical axis 53 of the drip chamber 13 disposed within the sensor gap 31. A plateau or flat surface 54 is provided on top of the mounting member 33 to engage the undersurface 48 of extension 24 and vertical stops 55 and 56 are provided on the edge of plateau 54 to limit the rotational horizontal movement between the sensor housing 26 and drip chamber 13 when the plateau 54 contacts the undersurface 48.

FIGS. 2 and 6-10 illustrate the inclined guiding surfaces 41 and 42 and the inclined projecting guide element 43 provided on the movable mounting member 34. These guiding surfaces diverge in the upward direction away from the longitudinal axis 53 of the drip chamber 13 when it is properly positioned within the sensor gap 13. The angle of camming surfaces 41 and 42 with respect to longitudinal axis 53 increase at the upper portion thereof in order to aid in guiding the mounting member upwardly so the inclined projecting guide or rib 43 will properly mate with the notch 44 at the end 46 of the extension 24. This enables the stopping element 60 or overhang 60 to engage the top surface 61 of the cantilevered extension 24. Ledge 57 is provided as a stop to control the rotation of the drop sensor with respect to the channel 13 in the plane of FIG. 6.

Figure 7:
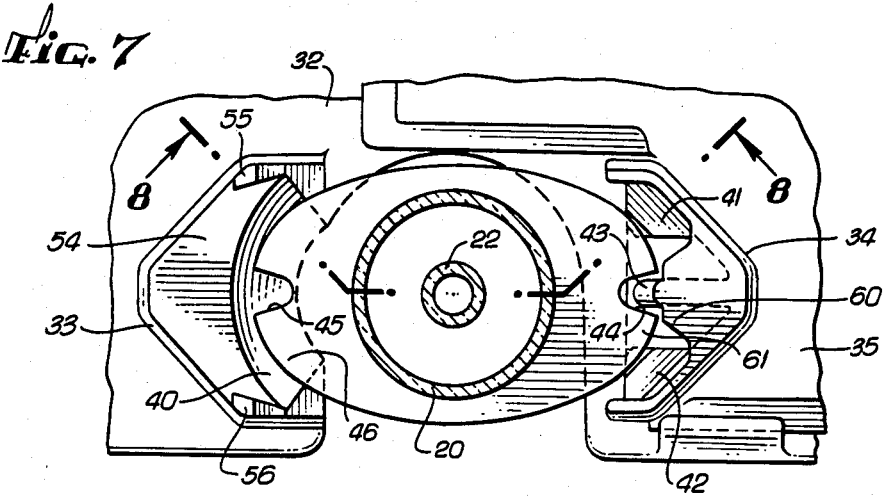
FIG. 7 is a plan view further illustrating the initial stages of mounting the drop sensor to the drip chamber.
Figure 8:
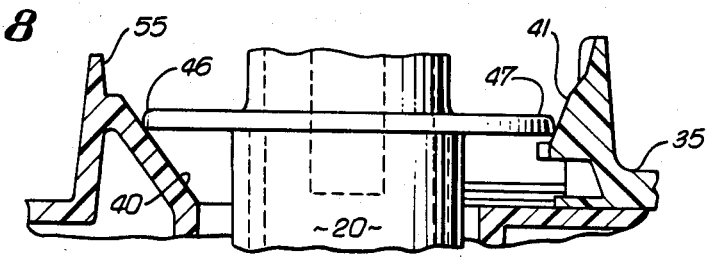
FIG. 8 is an elevational view, partially in section, taken along the lines 8—8 shown in FIG. 7 illustrating the inclined guiding surfaces.
Figure 9:
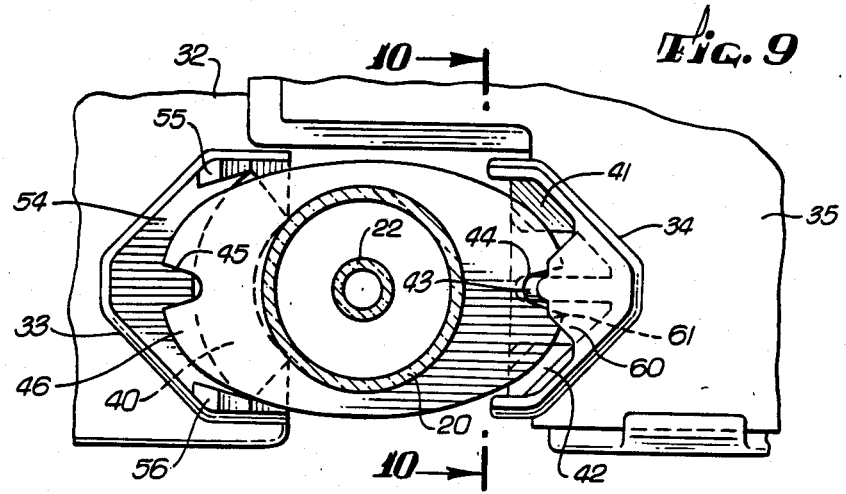
FIG. 9 is an enlarged plan view of the drop sensor mounted on the drip chamber.
Figure 10:
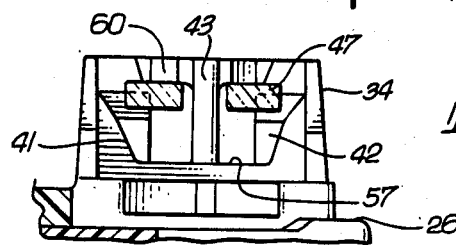
FIG. 10 is a sectional view taken along the lines 10—10 shown in FIG. 9.

The method of mounting or coupling of the drop sensor 25 to the drip chamber 13 is best illustrated in sequence of drawings 6-10. FIGS. 6 and 7 show the positioning of the sensor 25 about the drip chamber 13 during the initial stage of mounting with the cantilevered lateral extensions 24 cradled by the inclined guiding surfaces 40-43 on mounting members 33 and 34. The sleeve 35 is shown in its maximum open position to ensure that the ends 46 and 47 of the extensions 24 are properly cradled by the inclined camming surfaces on members 33 and 34.

When the spring loaded sleeve 35 is released, the guiding surfaces 40, 41 and 42 slidably engage the edges of extensions 24 and projecting guide element or rib 43 slides within the notch 44 provided at the end 47 of the extension 24 to thereby guide drop sensor 25 to a proper final position with the overhang 60 contacting the top surface 61 of the end 47 of extension 14, the plateau 54 contacting the undersurface 58 of the end 46 of extension 24 and the positioning vertical surfaces 50 and 51 on sensor housing 26 resting against the clear plastic cylindrical wall 62 of drip chamber body 20. Proper positioning of the drop sensor on the drip chamber 13 ensures that the drops of fluid 63 dripping from the drop former 23 into the chamber 13 (as shown in FIG. 4) will intercept the optical path 52 between the light sensor 27 and the light source 29 and will thereby be detected.

It is evident that the mounting means of the present invention provides for a simplified mounting of the drop sensor to the drip chamber. Moreover, once the drop sensor is in position, the vertical, horizontal and rotational movement thereof with respect to the drip chamber is restricted so that accidental contact does not misalign the drop sensor on the drip chamber.

It should be appreciated that a wide range of modifications and improvements can be made to the present invention without departing from the scope thereof.

I claim:

1. A system for monitoring the flow of parenteral fluid to a patient through a fluid administration set which includes a drip chamber having an elongated, clear plastic body with means to drip parenteral fluid therein and having a pair of opposed lateral extensions at the upper portion thereof, the system comprising:

a. a drop sensor having a housing with a first section at one end thereof containing a light source, a second section at the other end thereof containing a light sensor, and a sensor gap provided between the first and the second housing sections which has an optical pathway between the light source and the light sensor and which is adapted to receive the elongated, clear plastic body of the drip chamber;

b. a fixed mounting member on one of said housing sections having one or more vertically inclined guiding surfaces which engage the end of one of the lateral extensions on the drip chamber and slide under the edges of the end of the extension during the mounting of the drop sensor to the drip chamber and having vertically and horizontally oriented means at the end of such guiding surfaces to engage the lateral extension on the drip chamber in contact therewith and position the fixed mounting member with respect thereto;

c. a laterally movable mounting member on the other housing section having means to urge the movable mounting member toward the fixed mounting member, having one or more vertically inclined guiding surfaces divergently oriented to the inclined surfaces of the fixed mounting member which engage the end of the other lateral extension of the drip chamber and which slide under the edges of the lateral extension of the drip chamber when the drop sensor is mounted thereto and having means at the ends of the inclined guiding surfaces to engage the lateral extension on the drip chamber in contact therewith and position the movable mounting member with respect thereto;

d. at least one of the lateral extensions on the upper portion of the drip chamber having a notch or recess on the end thereof;

e. at least one of the vertically inclined guide surfaces comprising a projecting rib which interfits into the notch or recess provided in the lateral extension of the drip chamber; and f. a positioning surface on the drop sensor housing facing the sensor gap which contacts the elongated, clear plastic body of the drip chamber to ensure that drops of parenteral fluid dripping into the drip chamber intersect an optical pathway through the drip chamber body between the light source and the light sensor of the drop sensor.

2. The system of claim 1 wherein the mounting members are provided with inclined guiding surfaces which diverge in an upward direction away from the vertical axis of the drip chamber positioned within the sensor gap.

3. The system of claim 2 wherein the laterally movable mounting member is provided with at least a pair of inclined surfaces which engage the edge of the end of the lateral extension and which are provided with stopping means at the ends of said inclined surfaces to thereby terminate further relative movement therebetween and position the housing section.

4. The system of claim 1 wherein the laterally movable mounting member is attached to a sleeve which is slidably mounted to the drop sensor housing.

5. The system of claim 1 wherein the inclined surface on the fixed mounting member is a conic surface.

6. The system of claim 1 wherein the shape of the positioning surface on the drop sensor housing conforms to the shape of the drip chamber body.

7. The system of claim 1 wherein the shape of the drip chamber body is cylindrical.

8. The system of claim 2 wherein the distance between the inclined guiding surface or surfaces on the fixed mounting member and the inclined guiding surfaces on the movable mounting member in the latter's most distant position from the former is greater than the distance between the ends of the opposing lateral extensions on the drip chamber to thereby ensure that the inclined surfaces on both mounting members cradle the lateral extensions on the drip chamber during the initial stages of mounting the drop sensor to the drip chamber.

9. The system of claim 1 wherein the positioning surface on the drop sensor adapted to contact the drip chamber body is vertically spaced from the inclined surfaces on the mounting members.

10. The system of claim 1 wherein the horizontal means to engage and position the fixed mounting member is a plateau on the top thereof which contacts the underside of the lateral projection on the drip chamber.

11. The system of claim 10 wherein the vertically oriented means to engage and position the fixed mounting means are vertically oriented stopping means at the edge of the plateau to restrict relative horizontal movement between the fixed mounting member and the lateral extension of the drip chamber in contact therewith.

12. The system of claim 1 wherein the means on the movable mounting member to engage and fix the position thereof relative to the end of the lateral extension of the drip chamber is an overhang which is adapted to contact the upper surface of the lateral extension.

13. A system for monitoring the flow of fluid to a patient which includes a drip chamber and a drop sensor provided with mating mounting elements to ensure that only matched drip chambers and drop sensors are utilized together, said system comprising:

a. the drip chamber having an elongated, clear plastic body and provided with a pair of opposed lateral extensions at the upper portion thereof, at least one of the lateral extensions having one or more notches or recesses at the end thereof; and b. a drop sensor having a housing with a first section at one end thereof containing a light source, a second section at the other end thereof containing a light sensor, and a sensor gap provided between the first and the second housing sections which has an optical pathway between the light source and the light sensor and which is adapted to receive the elongated, clear plastic body of the drip chamber;

c. a fixed mounting member on one of said housing sections having one or more vertically inclined guiding surfaces which engage the end of one of the lateral extensions on the drip chamber and slide under the edges thereof during the mounting of the drop sensor to the drip chamber and having vertically and horizontally oriented means at the end of such guiding surfaces to engage and position the fixed mounting member with respect to the lateral extension on the drip chamber in contact therewith;

d. the laterally movable mounting member on the other housing section having means to urge the movable mounting member toward the fixed mounting member, having one or more vertically inclined guiding surfaces divergently oriented to the inclined surfaces of the fixed mounting member which engage the end of the other lateral extension of the drip chamber and which slide under the edges of the lateral extension when the drop sensor is mounted to the drip chamber and having means at the ends of the inclined guiding surfaces to engage and fix the position of the movable mounting member with respect to the lateral extension on the drip chamber in contact therewith;

e. at least one of the vertically inclined guide surfaces on the mounting members comprising a projecting rib which interfits a recess provided in the lateral extension; and f. a positioning surface on the drop sensor housing facing the sensor gap which contacts the elongated, clear plastic body of the drip chamber to ensure that drops of parenteral fluid dripping into the drip chamber intersect the optical pathway through the drip chamber body between the light source and the light sensor of the drop sensor.

14. The system of claim 13 wherein the inclined projecting rib is positioned on the laterally movable mounting member between two inclined guiding surfaces provided thereon.

15. The system of claim 14 wherein the laterally movable mounting member is attached to a sleeve which is slidably mounted to the drop sensor housing.

16. The system of claim 14 wherein stopping means are provided at the upper end of the inclined rib to terminate further relative vertical movement therebetween.

17. The system of claim 15 wherein the horizontally oriented means to engage and position the fixed mounting member is a plateau on the top thereof which contacts the underside of the lateral projection on the drip chamber and the vertically oriented means to engage and position the fixed member are vertically oriented stopping means at the edge of the plateau to restrict rotational and horizontal movement between the fixed mounting member and the lateral extension in contact therewith.

18. The system of claim 17 wherein the stopping means at the upper end of the inclined projecting rib is an overhang which is adapted to engage the upper surface of the lateral projection on the drip chamber and thereby preclude further movement.

19. The system of claim 3 wherein the projecting rib is positioned between the pair of inclined surfaces.

* * * * *